United States Patent
Hauri et al.

(10) Patent No.: US 9,216,097 B2
(45) Date of Patent: Dec. 22, 2015

(54) LIGAMENT-TENSIONING DEVICE

(75) Inventors: Thomas Hauri, Staffelbach (CH); Jan Stifter, Schneisingen (CH)

(73) Assignee: Smith and Nephew Orthopaedics AG, Rotkreuz (CH)

( * ) Notice: Subject to any disclaimer, the term of this patent is extended or adjusted under 35 U.S.C. 154(b) by 1773 days.

(21) Appl. No.: 12/090,850

(22) PCT Filed: Oct. 18, 2006

(86) PCT No.: PCT/EP2006/010052
§ 371 (c)(1),
(2), (4) Date: Oct. 22, 2008

(87) PCT Pub. No.: WO2007/045460
PCT Pub. Date: Apr. 26, 2007

(65) Prior Publication Data
US 2009/0222089 A1     Sep. 3, 2009

(30) Foreign Application Priority Data
Oct. 18, 2005 (DE) .......................... 10 2005 049 851

(51) Int. Cl.
*A61B 17/58* (2006.01)
*A61F 2/46* (2006.01)
(Continued)

(52) U.S. Cl.
CPC .............. *A61F 2/4657* (2013.01); *A61B 17/025* (2013.01); *A61B 2017/0268* (2013.01);
(Continued)

(58) Field of Classification Search
CPC ...... A61B 17/02; A61B 17/025; A61B 17/66; A61B 2017/0268; A61B 2017/681
USPC .......... 606/86 R, 87, 88, 90, 102; 623/13.13, 623/17.13
See application file for complete search history.

(56) References Cited

U.S. PATENT DOCUMENTS

| | | | |
|---|---|---|---|
| 4,501,266 | A | 2/1985 | McDaniel |
| 4,997,432 | A | 3/1991 | Keller |

(Continued)

FOREIGN PATENT DOCUMENTS

| | | |
|---|---|---|
| DE | 22 53 929 | 5/1973 |
| DE | 38 09 793 | 3/1988 |

(Continued)

OTHER PUBLICATIONS

International Search Report for related PCT Application No. PCT/EP2006/010052, mailed Apr. 12, 2007, 11 pages.

(Continued)

*Primary Examiner* — Matthew Lawson
(74) *Attorney, Agent, or Firm* — Taft Stettinius & Hollister LLP

(57) ABSTRACT

A ligament-tensioning device for activation of the ligament and/or capsule system in the implantation of a joint implant, comprising a distal bearing plate for bearing against a distal skeletal part and comprising first and second proximal bearing plates, each of which partially overlaps the distal bearing plate in a first in-use position, for bearing against a proximal skeletal part, and comprising means for relative displacement of the proximal bearing plates to increase their spacing from the distal bearing plate. The displacement means comprise a scissor-type guide means that supports the respective proximal bearing plate in the ventral-dorsal as well as the medial-lateral parallel position with respect to the distal bearing plate.

48 Claims, 7 Drawing Sheets

(51) Int. Cl.
*A61B 17/02* (2006.01)
*A61F 2/38* (2006.01)

(52) U.S. Cl.
CPC ............... *A61F 2/38* (2013.01); *A61F 2/4684* (2013.01); *A61F 2002/4624* (2013.01); *A61F 2002/4661* (2013.01)

(56) References Cited

U.S. PATENT DOCUMENTS

| | | | |
|---|---|---|---|
| 5,540,696 A * | 7/1996 | Booth et al. | 606/88 |
| 6,056,756 A | 5/2000 | Eng et al. | |
| 6,251,067 B1 | 6/2001 | Strickholm | |
| 7,309,357 B2 * | 12/2007 | Kim | 623/17.13 |
| 2003/0069644 A1 * | 4/2003 | Kovacevic et al. | 623/20.32 |
| 2004/0097951 A1 * | 5/2004 | Steffensmeier | 606/102 |
| 2005/0020941 A1 * | 1/2005 | Tarabichi | 600/587 |
| 2005/0177170 A1 | 8/2005 | Fisher et al. | |
| 2006/0111790 A1 * | 5/2006 | Dietz | 623/20.32 |
| 2006/0149277 A1 | 7/2006 | Cinquin et al. | |
| 2008/0091209 A1 | 4/2008 | Schmotzer et al. | |

FOREIGN PATENT DOCUMENTS

| | | |
|---|---|---|
| DE | 203 20 501 | 12/2004 |
| DE | 103 48 585 | 4/2005 |
| GB | 1 386 828 | 3/1975 |
| WO | WO 00/78255 | 12/2000 |
| WO | WO 2004/078047 | 9/2004 |

OTHER PUBLICATIONS

English Translation of International Preliminary Report on Patentability for related PCT Application No. PCT/EP2006/010052, mailed Apr. 29, 2008, 12 pages.

* cited by examiner

LIGAMENT-TENSIONING DEVICE

CROSS-REFERENCE TO RELATED APPLICATIONS

This Application is a US National Phase of the International Application No. PCT/EP2006/010052 filed Oct. 18, 2006 designating the US and published in German on Apr. 26, 2007 as WO 2007/045460, which claims priority of German Patent Application No. 10 2005 049 851.5, filed Oct. 18, 2005.

BACKGROUND OF THE INVENTION

1. Field of the Invention

The invention relates to a ligament-tensioning device for activation of the ligament and/or capsule system in the implantation of a joint implant.

2. Description of the Related Art

Other ligament-tensioning devices having a similar function are known. For example, WO 00/78225 A1 discloses a ligament-tensioning device which, in addition to having a prismatic, cylindrical or plate-shaped base body, which has a bearing surface for bearing against a first bone adjoining a non-spherical joint, has right and left tensioning levers having second bearing surfaces which are to be applied to the joint-side surface of a second bone adjoining the joint, the operation of associated handgrips and operating levers being co-ordinated. The opposing portions (bearing surfaces) are supported with respect to one another by four-bar lever mechanisms.

DE 103 48 585 A1 discloses a further ligament-tensioning device which comprises a first, distal bearing plate for bearing against a first skeletal part and a second, proximal bearing plate for bearing against a second skeletal part, the two bearing plates being displaceable relative to one another by a hydraulic drive means and, especially, being tiltable relative to one another by means of a central axis. In addition, they are joined to one another by means of a base body, the distal bearing plate in particular being joined rigidly thereto.

WO 2004/078047 A1 discloses a further ligament-tensioning device, which comprises a distal bearing plate and two proximal bearing plates independently guided and displaceable relative thereto. Guidance is effected therein in each case by means of a double hinge connection and the drive is preferably likewise effected hydraulically.

According to current experiences, the known ligament-tensioning devices still have certain disadvantages in use. Those disadvantages relate especially to the desired exact alignment between the opposing bearing plates and to the expense associated with a hydraulic drive device. In addition, when the known ligament-tensioning devices are used, the joint in question has to be kept open, because substantial parts of the device protrude.

SUMMARY OF THE INVENTION

One embodiment of the invention therefore addresses the problem of providing an improved ligament-tensioning device having a wide variety of possible applications that is economical and reliably satisfies the requirements of practice.

In accordance with another embodiment of the invention, a ligament-tensioning device for activation of a ligament and/or capsule system in the implantation of a joint implant is provided. The device can have a distal bearing plate for bearing against a distal skeletal part. The device can further have first and second proximal bearing plates, each of which partially overlapping the distal bearing plate in a first in-use position, for bearing against a proximal skeletal part. The device can further have means for relative displacement of the proximal bearing plates to increase their spacing from the distal bearing plate. Additionally, all the components of the ligament-tensioning device can be dimensioned to be accommodated between portions of the distal and proximal skeletal parts adjacent the joint in such a way that a joint capsule can be closed again after insertion of the ligament tensioning device. The components accommodated can include the distal bearing plate, the first bearing plate, and/or the second bearing plate. Further possible aspects of such a ligament-tensioning device are included in the description herein.

Some embodiments of the invention can further provide a ligament-tensioning device that is fully insertable into the joint in question, thus making it possible to close the joint capsule again after insertion. For that purpose, in particular the bearing plates are to be dimensioned to match the joint in question—for example a knee joint—and projecting parts (such as, for example, handgrips/levers or hydraulic lines which project in the prior art) are generally to be avoided. In that respect some embodiments of the invention can include the concept of providing a purely internal drive means or internal displacement means for the relative displacement of the opposing bearing plates.

In one embodiment, the invention provides parallel guidance between the distal bearing plate and the proximal bearing plates that is precise in both the ventral-dorsal and the medial-lateral directions. This can be realized especially advantageously by a suitable guide means in accordance with the scissors principle. Other two-plane parallel guide means also can be used, however, for example the use of two hinge joints that are not axially parallel to one another (especially enclosing an angle of 90° with respect to one another).

In further embodiments, the invention can also include the concept of providing, as drive means for pushing the distal bearing plate and the proximal bearing plates apart from one another, a separate drive element in each case, that drive element being, moreover, a drive element that functions without auxiliary energy. In these embodiments, the invention can assign to each proximal bearing plate a spring element which, in a starting state in which the proximal bearing plate is spaced a minimum distance apart from the distal bearing plate, can store the drive energy and release it for the purpose of increasing the spacing when the ligament-tensioner is brought into operation. In a further embodiment, the invention can also include the concept of assigning to that spring element or to the opposing bearing plates a locking means for releasable fixing in the starting position.

In principle, however, a drive means having auxiliary energy, for example an electromotive, electromagnetic, hydraulic or pneumatic drive means, also comes into consideration. Such a drive means can drive both proximal bearing plates jointly, it being possible for the bearing plates to take up different end positions in force equilibrium with the surrounding capsule/ligament structure. The said drive means can, however, also be provided separately for each proximal bearing plate.

It should be pointed out here that the terms "distal bearing plate" and "proximal bearing plate" are used herein with reference to preferred in-use positions of the ligament-tensioner, for example when used in the knee. For that application, it is also possible to speak synonymously of a tibia bearing plate and a femur bearing plate, respectively; the invention is also to be understood, however, as potentially including transpositions of the bearing plates in respect of their position further from or closer to the center of the body (distal or proximal, respectively).

In further embodiments, the spring element can have a compression spring element which is arranged in a region of overlap between the proximal and distal bearing plates and supported against both, the spring element having, for example, a steel or titanium helical spring having a suitable spring characteristic. The spring can have a spring constant matched to a predetermined tensioning force in order to provide, for example, a tensioning force that is substantially constant over its travel in the range between 50 and 90 N, especially 70 N.

To realise a relatively high and constant tensioning force and realise a small initial height of the spring element in the tensioned state, the device can use special forms of the compression springs tailored thereto. In one embodiment, the steel or titanium helical spring for increasing the travel is of conical or double-cone form and, especially, has a pitch indirectly proportional to the local winding diameter. The conical shape of the spring element can be chosen so that the overall height in the tensioned state is substantially less than that of a comparable helical spring having a cylindrical basic shape.

In an alternative embodiment, the spring element can have a flexural spring element, more specifically, for example, a steel spiral or leaf spring.

The scissor-type guide means can have two scissor joints arranged close to opposite ends of the proximal bearing plate, that is to say spaced as far apart from one another as possible. In various embodiments of the invention it is possible for those scissor joints to be arranged in the ventral-dorsal direction (one behind the other) or in the medial-lateral direction (one next to the other). In one embodiment of the scissor-type guide means, the ends of the scissor joints can be inserted in grooves in the distal and proximal bearing plates and a limb or an end of each of the two limbs is rotatably fixed therein by means of bearing pins extending perpendicular to the run of the groove.

Additionally improved guidance and fixing to one another of the opposing bearing plates is obtained by providing at each end of the free limb or at the free end of each of the two limbs a slide peg for guiding the respective limb or end in a groove formed to match the slide peg. To increase the rigidity and to provide even better guidance, the scissor joints are preferably also joined to one another by means of at least one connecting rod mounted at the end of a limb of each scissor joint.

For adaptation to the specific anatomical conditions of different patients, the first and second proximal bearing plates each comprise an upper and a lower part, the lower part being provided with means for mounting the spring element and the scissor-type guide means and the upper part being fixed releasably on the lower part to increase the thickness of the bearing plate in question. The ligament-tensioning device can be used with a set of upper parts of different thicknesses to provide an especially precise solution to the mentioned adaptation problem.

The above-mentioned locking is advantageously released by the provision on the distal bearing plate or the first and second proximal bearing plates of releasable locking means for independent locking of the first and second proximal bearing plates to the distal bearing plate at a minimum spacing and with a maximum spring tension with respect thereto.

In some embodiments the locking means each have a hook pivotally mounted on the respective bearing plate and engaging in the opposing bearing plate, on which hook there is provided a first tool-engagement portion for actuation. The tool-engagement portion is preferably configured for engagement of a hex key tool, for example a 3.5 mm hex key.

In one embodiment of the locking means, having a pivotable hook, an engagement portion for that hook is formed in the material of the first and second proximal bearing plates in spatial association with the hook articulated on the distal bearing plate.

In an additional embodiment, a first bearing peg of a scissor joint of the first and second proximal bearing plates can project beyond the outer edge thereof and be so arranged relative to the hook pivotally mounted on the distal bearing plate that it forms a counter-bearing of the locking means. In that embodiment—or alternatively independently thereof—a second bearing peg of a scissor joint of the first and second proximal bearing plates projects beyond the outer edge thereof and is so arranged relative to the hook pivotally mounted on the distal bearing plate that it forms the hinge pin thereof.

Since, on account of the high forces necessary, a tool is also advantageously used for positioning the ligament tensioner at the site of use, a second tool-engagement portion, especially a cylindrical recess, is preferably provided on the side edges of the distal bearing plate and of the first and second proximal bearing plates for engagement of a positioning tool. The provision of a separate tool is especially advantageous with a view to realising a ligament tensioner that can be fully integrated into a joint.

A further embodiment provides a construction for the releasable coupling-on of a sizer, which couples the proximal and distal skeletal parts in flexion to facilitate axis transmission from the one skeletal part to the other, taking account of the ligament tension. In principle, the coupling-on includes simply being in contact with suitably prepared bearing surfaces, but it also includes connecting means for fixing the sizer on the distal bearing plate. In some embodiments, the connecting means can comprise two clip-like extensions on the distal bearing plate which, each engaging around a side edge of the proximal bearing plates, run to a base plate of the sizer.

Arrangements comprising the proposed ligament-tensioning device and a matching positioning tool and/or a sizer matched thereto are also to be regarded as being included in the scope of protection of the invention.

BRIEF DESCRIPTION OF THE DRAWINGS

Advantages and functional features of the invention will otherwise be found in the following description of preferred example embodiments with reference to the Figures.

DETAILED DESCRIPTION OF THE PREFERRED EMBODIMENTS

Figure 1:
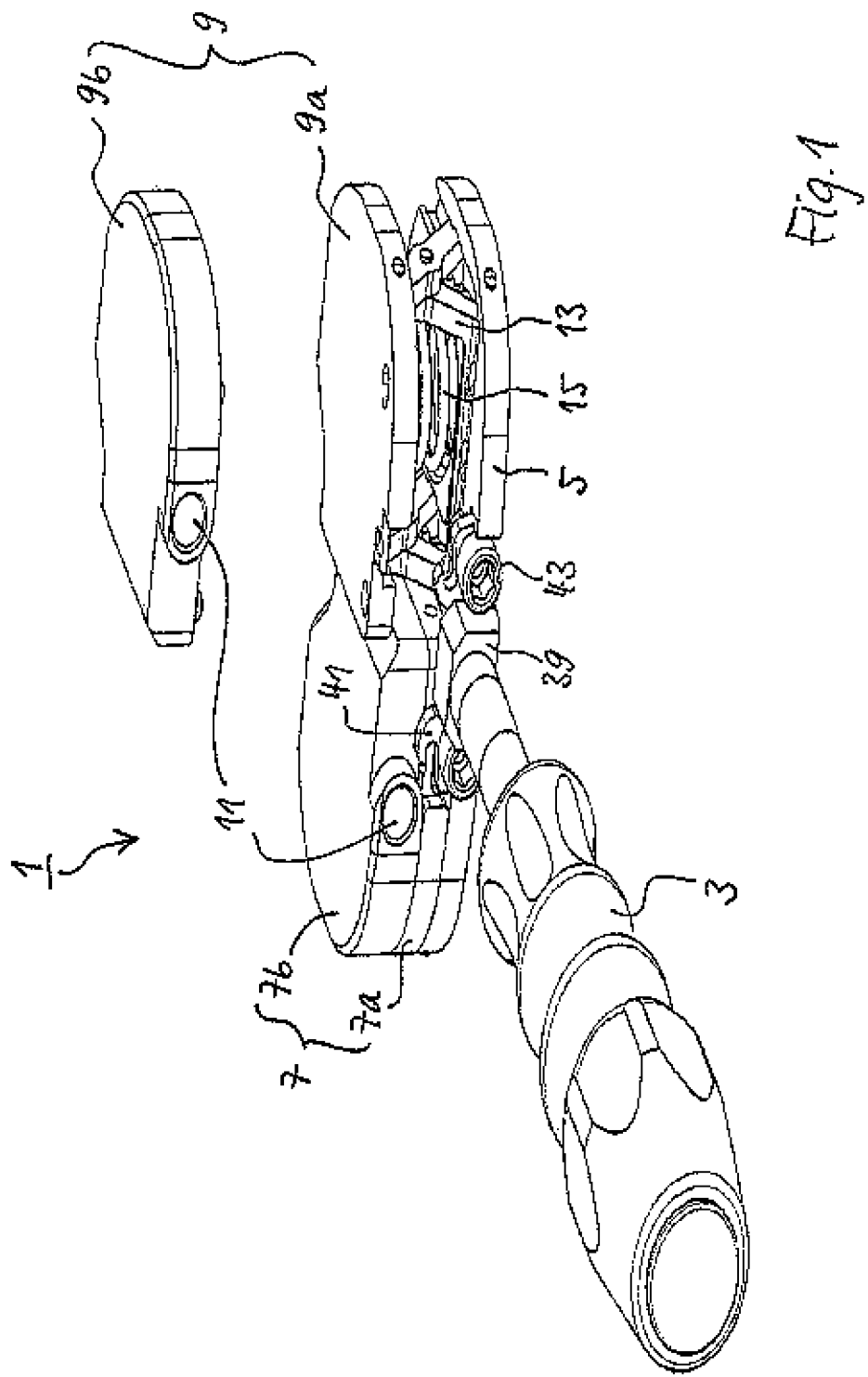
FIG. 1 is a perspective view of a ligament-tensioning device according to one embodiment of the invention ventrally obliquely from above, partly as an exploded view, with an attached positioning tool.

FIGS. 1-4 show various views of an embodiment of a ligament-tensioning device 1 in various states (described below), with FIG. 1 showing the device co-operating with a positioning tool.

Figure 2:
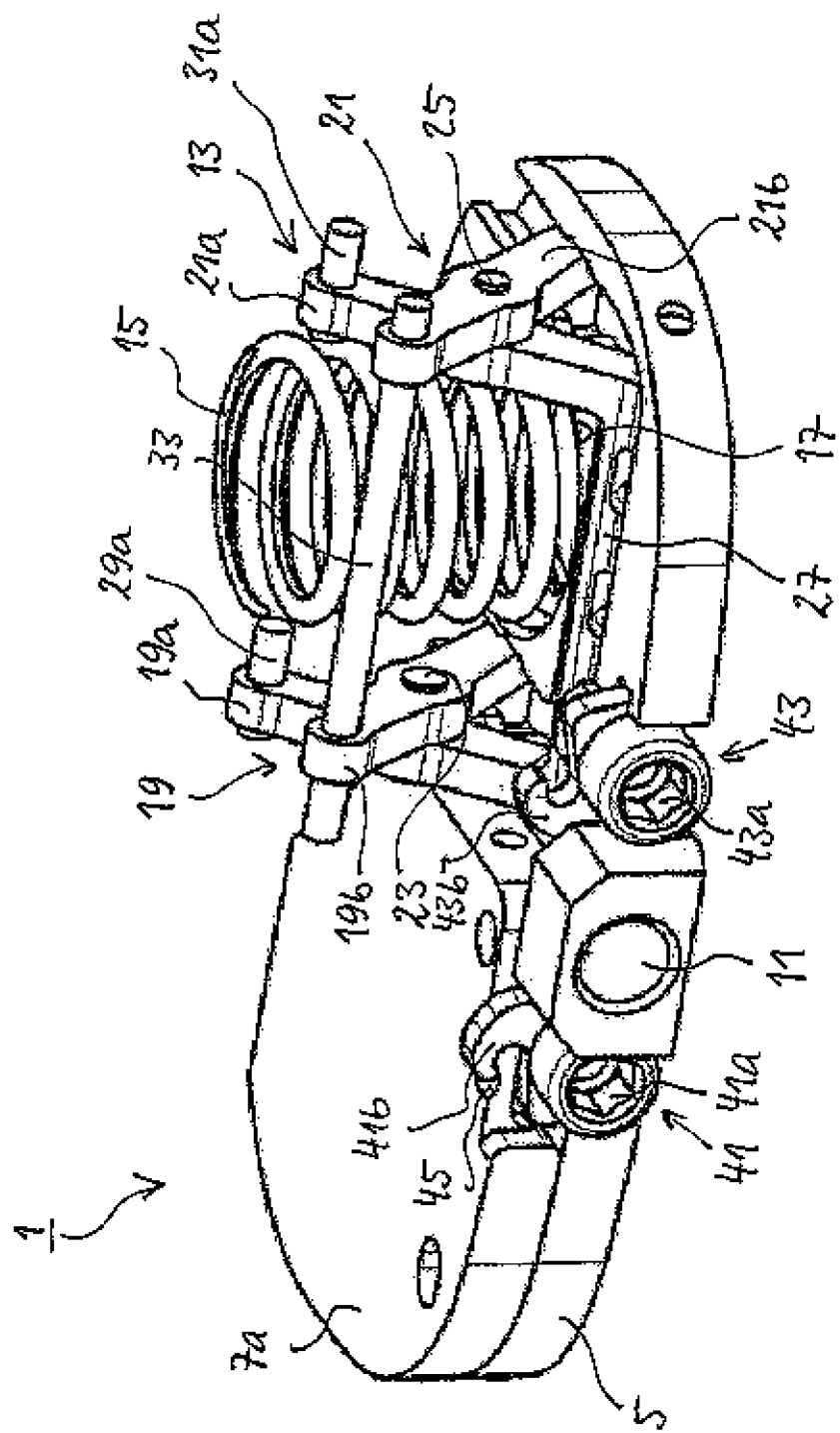
FIG. 2 is a perspective view of the ligament-tensioning device according to FIG. 1 ventrally obliquely from above, with the second proximal bearing plate removed and the associated displacement means in the fully extended state.

The ligament-tensioning device 1 comprises a distal bearing plate 5, which is approximately kidney-shaped in plan view, and, arranged in parallel therewith and opposite thereto, two proximal bearing plates 7 and 9 each of which overlaps approximately half of the distal bearing plate, the proximal bearing plates each comprising a lower part 7a, 9a and an upper part 7b, 9b. For positioning the ligament-tensioning device 1 with the aid of the positioning tool 3 there are provided on the front side edges of the distal and proximal bearing plates respective cylindrical recesses 11 as engagement portions (FIG. 1 shows the recesses in the proximal bearing plates, more specifically in the upper parts 7b, 9b thereof, while FIG. 2 shows the central recess 11 in the distal bearing plate 5).

The proximal bearing plates 7 and 9 (or, more specifically, the lower parts 7a, 9a thereof) are joined to the illustrated device 1 by means of a scissor-type guide means 13 and are tensioned against the device by a steel compression spring 15 as spring element. As can be seen most clearly in FIGS. 2 and 3, the helical spring 15 is seated in a matching circular recess 17 on the upper side of the distal bearing plate 5; a similar mounting (not shown) is provided on the underside of the respective associated proximal bearing plate.

The scissor-type guide means 13 comprises medial and lateral scissor joints 19, 21 which each comprise two limbs 19a, 19b and 21a, 21b pivotally connected by means of a hinge pin 23, 25, respectively. The limbs 19a, 21a are joined to one another at one end by means of an integrally formed bridge or connecting bar 27, while a slide peg or pin 29a, 31a is inserted in their other end for connection to the lower part 9a (omitted in FIGS. 2 and 3) of the second bearing plate. In a similar way, one end of each of the limbs 19b, 21b can be joined by means of a connecting rod 33 inserted perpendicular to the plane of extension, which rod projects beyond the medial or lateral outer side of the respective limb and forms further slide pegs (not shown separately) there.

Figure 3:
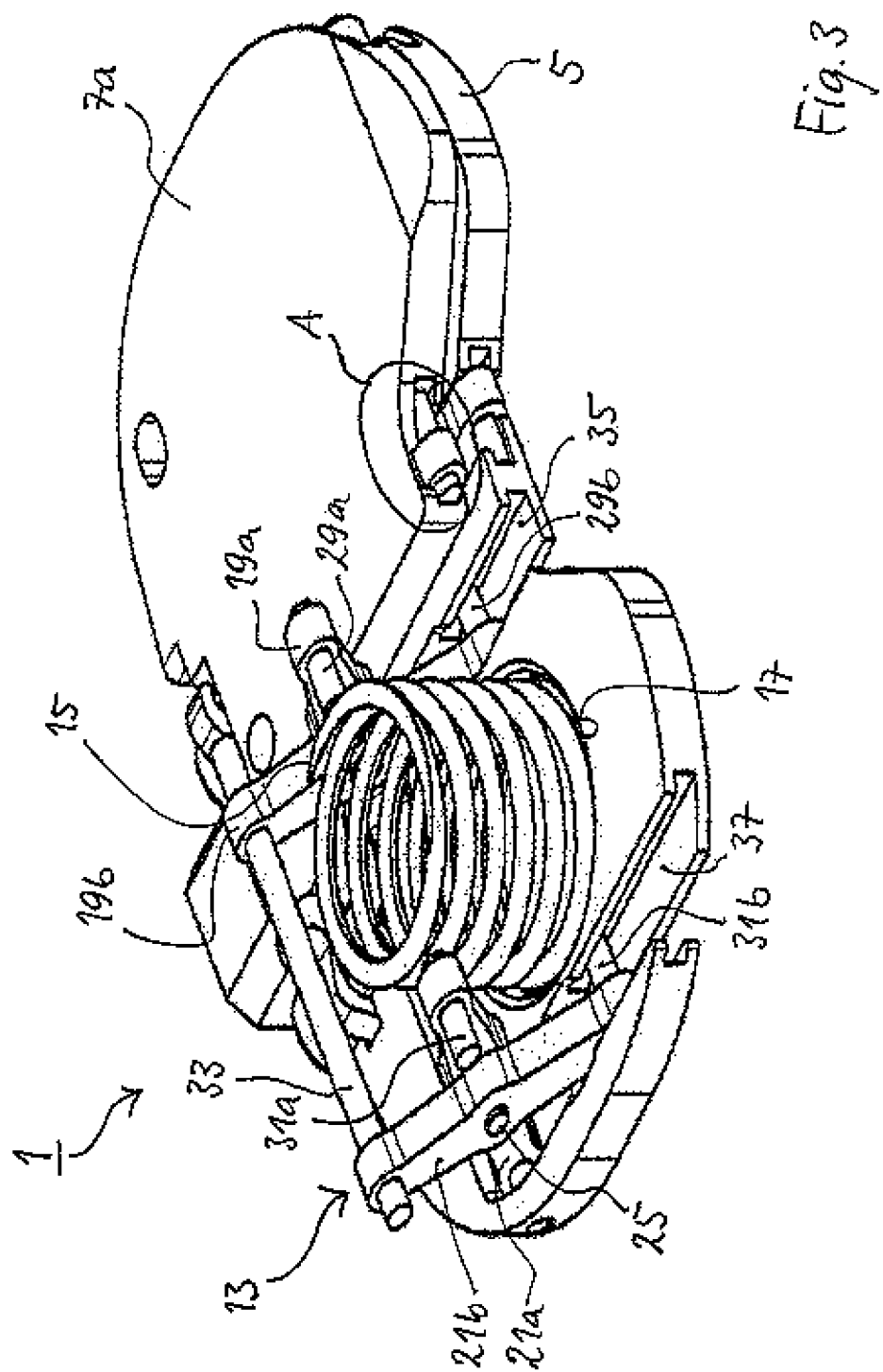
FIG. 3 is a perspective view of the ligament-tensioning device according to FIG. 1, with the second proximal bearing plate removed and the displacement means in an intermediate position, dorsally obliquely from above.
Figure 4:
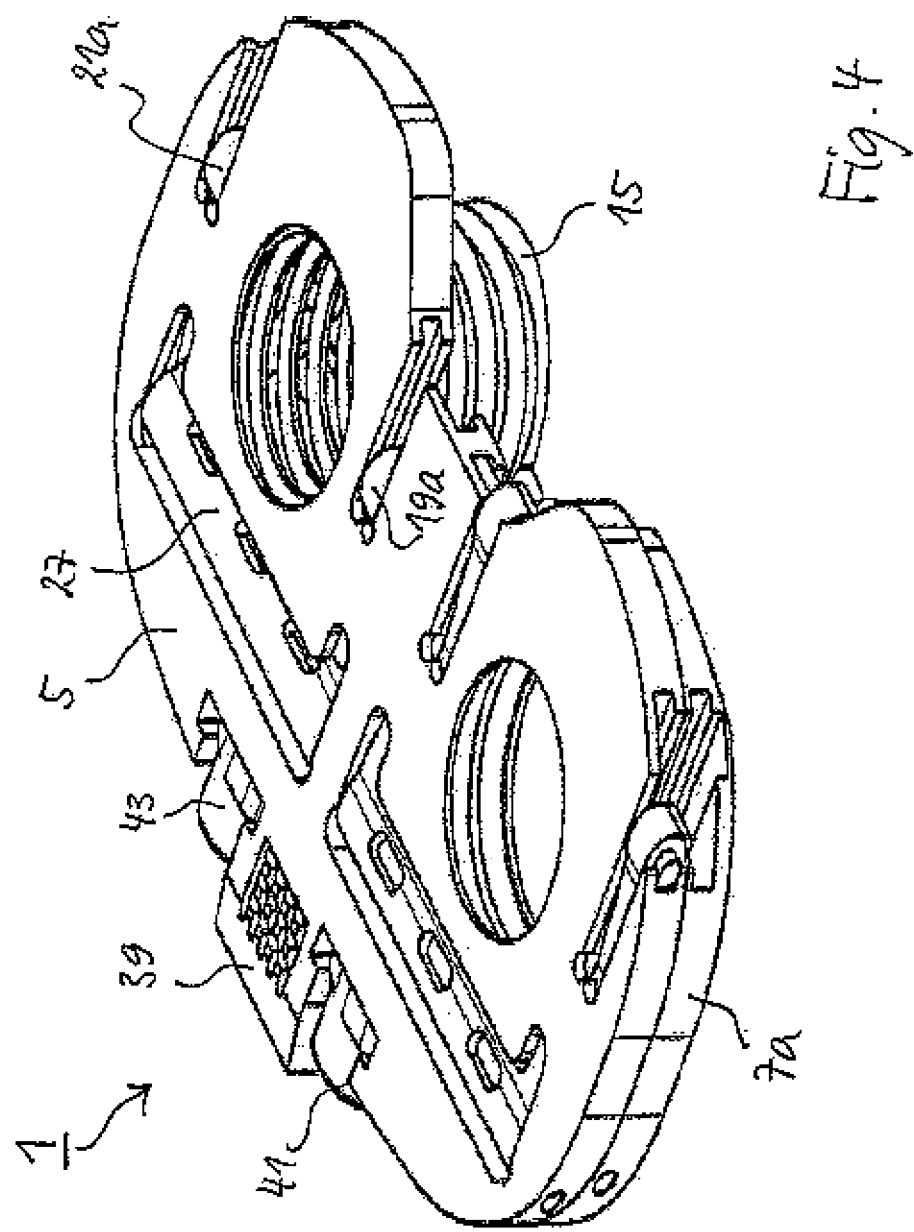
FIG. 4 is a perspective view of the ligament-tensioning device according to FIG. 1, with the second proximal bearing plate removed, ventrally obliquely from below.

The opposite ends of the limbs 19b, 21b are in turn each provided with a separate slide pin 29b, 31b, respectively. Those slide pegs 29b, 31b engage (as can be seen most clearly in FIG. 3) in correspondingly dimensioned grooves 35, 37 in the distal bearing plate 5 which, in the in-use position of the ligament-tensioning device, run dorsally-ventrally and fix the scissor-type guide means so as to be slidable therewith in the distal bearing plate 5. (As can be seen to some extent in the portion of FIG. 3 showing the lower part 7a of the first proximal bearing plate 7—see detail "A"—a corresponding groove structure, which does not have a separate reference numeral herein, is provided in the proximal bearing plates.)

As can be seen most clearly in FIG. 2, on the ventral side edge (front edge) of the distal bearing plate 5, on both sides of an extension containing the cylindrical recess 11 there are mounted two pivotable hook elements 41, 43, each of which comprises a hex key engagement portion 41a, 43a and an integrally formed hook portion 41b, 43b, respectively. As can be seen in FIG. 2 in the region of the first proximal bearing plate, the hook portions engage in a recess on the upper side of the respective bearing plate lower part, which recess is shaped to correspond to the shape of the hook, only the recess 45 in the lower part 7a of the first proximal bearing plate being shown in FIG. 2. By means of such engagement, the proximal bearing plates are held at a minimum distance from the distal bearing plate. By rotation of the respective hook element 41, 43 with a suitable tool, that locking is released and the proximal bearing plate in question can be moved away from the distal bearing plate under the bias of the associated compression spring 15 until its movement comes to a standstill in force equilibrium with the capsule/ligament tension acting at the site of use.

Figure 5:
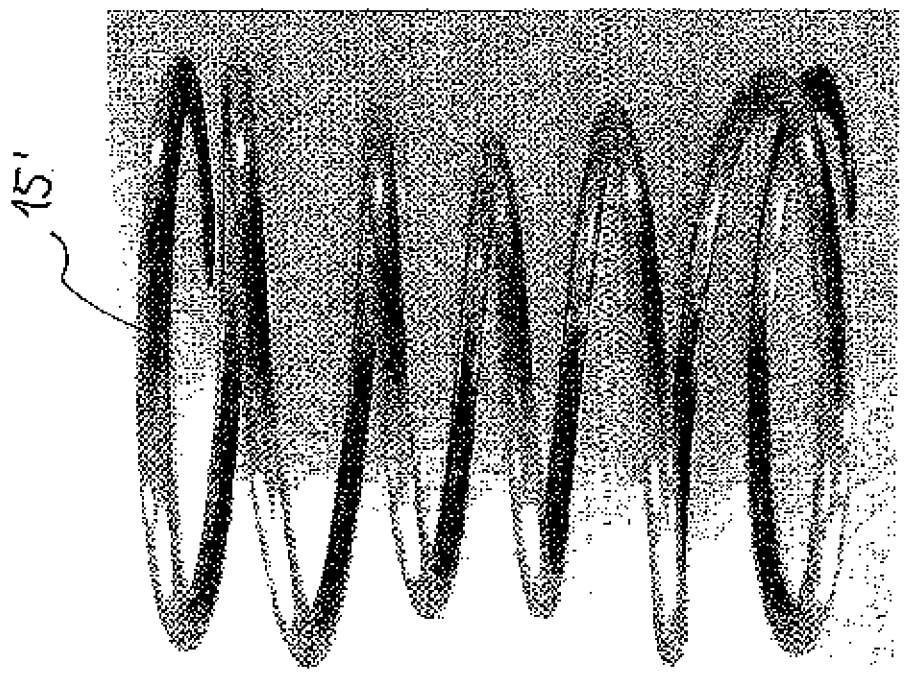
FIG. 5 is a perspective view of a helical spring suitable for use as spring element in the ligament-tensioning device according to FIG. 1, in a double-cone configuration.
Figure 6A:
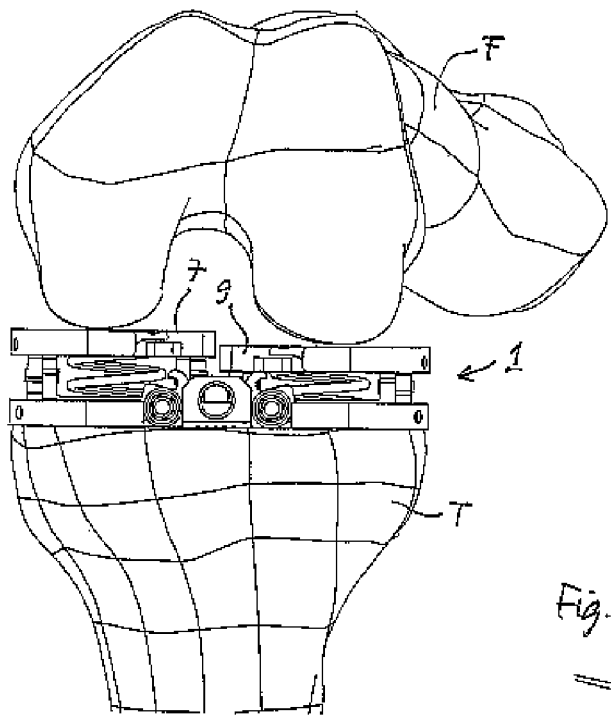
FIGS. 6A-6D show various views of the ligament-tensioning device according to FIG. 1 in its in-use state installed in a knee joint.
Figure 6B:
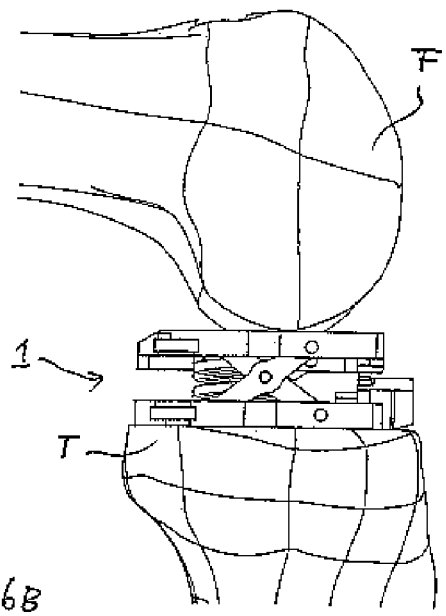
Figure 6C:
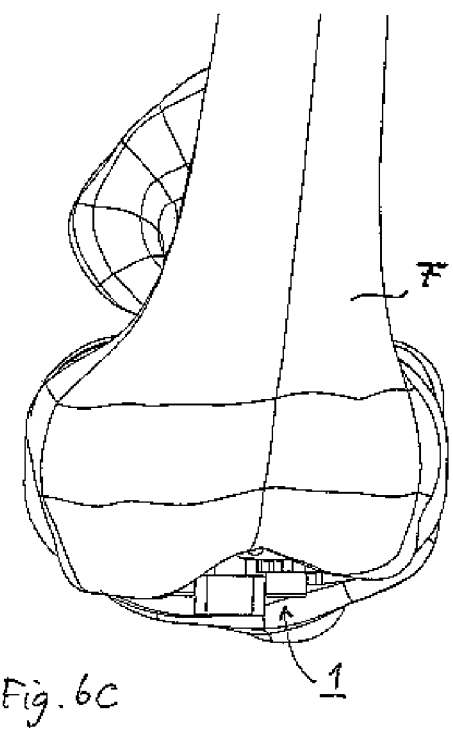
Figure 6D:
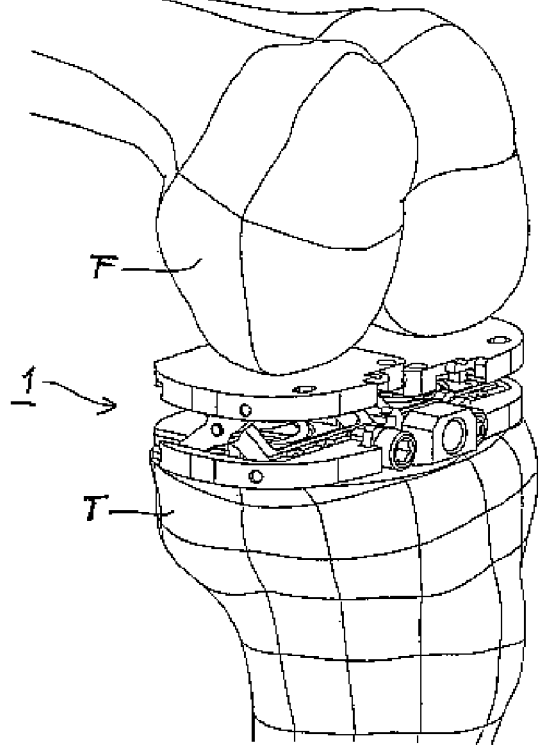
Figure 7A:
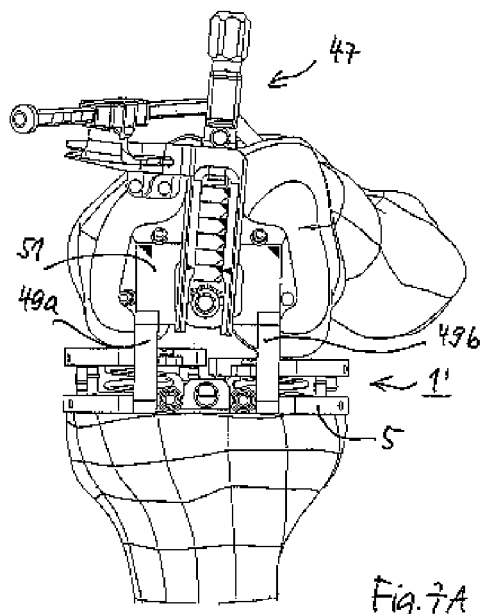
FIGS. 7A-7D show various views of the ligament-tensioning device according to FIG. 1 in its in-use state installed in a knee joint, with a coupled-on sizer.
Figure 7B:
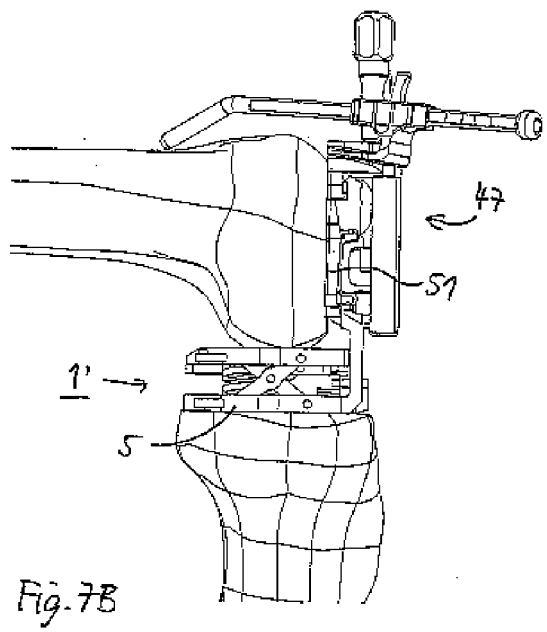
Figure 7C:
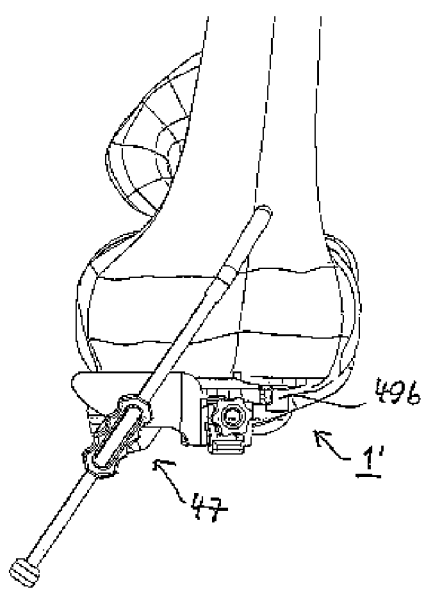
Figure 7D:
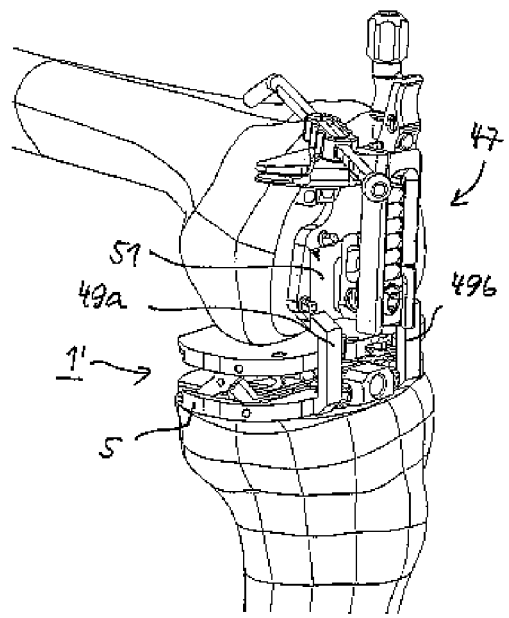

Whereas in FIGS. 1-4 a cylindrical helical spring 15 is shown as the spring element, FIG. 5 shows, as a modification, a double-cone helical spring 15' which, by virtue of its lesser overall height in the tensioned state, can be used preferably in the ligament-tensioning device 1 according to FIG. 1-4, it being possible (in a configuration not shown) for the pitch of the winding in the lower and upper regions of greater diameter to be smaller than in the central region, in order that a troublefree spring action is ensured over the entire travel.

The above-described ligament-tensioning device 1 is constructed for use in a knee joint and is shown in that in-use state in various views in FIGS. 6A to 6D. The Figures clearly show the matching of the dimensions, especially the length/width ratio, and the configuration of the two proximal bearing plates 7, 9 to the anatomical conditions of the knee joint and the overall dimensions and relative sizes of the tibia T and the (resected) femur F. As shown, the device can have a length/width ratio of approximately 3/2, in accordance with that of a proximal resected tibia.

FIGS. 7A to 7D show a diagrammatic view, comparable to FIGS. 6A-6D, of a modified configuration of a ligament-tensioning device 1' with a coupled-on sizer 47. Generally, a sizer serves for the intra-operative coupling of tibia and femur in flexion so that axis transmission of the tibial axis, taking account of the ligament tension, to the femur can be effected. It is accordingly possible, in accordance with an embodiment of the invention, to define the optimum size and position of a knee implant in the ventral-dorsal direction and in rotation. Attention should be drawn, to the provision of connecting means between the ligament-tensioning device 1' and the sizer 47, namely two clip-like extensions or connecting bars 49a, 49b on the distal bearing plate 5, which engage over the proximal bearing plates (not shown herein) at one side edge thereof and make a connection to a base plate 51 of the sizer 47.

The implementation of the invention is not confined to the embodiments described herein and the last-mentioned modification of the spring element, but is also possible in a multiplicity of embodiments which lie within the scope of the invention. For example, in particular an embodiment is possible having a scissor-type guide means which is turned through 90° with respect to the embodiment shown and in which some of the slide pegs or pins can be constructed simultaneously as bearing pins for the fixed positioning of a limb end in the associated bearing plate. In such an embodiment it is also possible for such a bearing pin to be used simultaneously as hinge pin of the pivotable locking hooks. Furthermore, in the case of the proximal bearing plates it is also possible for the upper parts to be omitted, and numerous degrees of freedom exist in respect of the exact shape and relative dimensions of the bearing plates.

LIST OF REFERENCE NUMERALS 1 ligament-tensioning device
2 positioning tool
5 distal bearing plate
7, 9 proximal bearing plates
7a, 9a lower parts of the proximal bearing plates
7b, 9b upper parts of the proximal bearing plates
11 cylindrical recess
13 scissor-type guide means
15 cylindrical helical spring
15' double-cone helical spring
17 circular recess
19 medial scissor joint
19a, 19b limbs of the medial scissor joint
21 lateral scissor joint
21a, 21b limbs of the lateral scissor joint
23 hinge pin of the medial scissor joint
25 hinge pin of the lateral scissor joint
27 connecting bar
29a, 29b, 31a, 31b slide pegs
35, 37 grooves
41, 43 hook elements
41a, 43a hex key engagement portions
41b, 43b integral hook portions
45 recess
47 sizer
49a, 49b extensions
51 base plate

What is claimed is:

1. A ligament-tensioning device for activation of a ligament and/or capsule system in the implantation of a joint implant, said device comprising:
    a distal bearing plate adapted to bear against a distal skeletal part;
    first and second proximal bearing plates, each of which at least partially overlaps said distal bearing plate when in a first in-use position, and adapted to bear against a proximal skeletal part;
    a displacer for relative displacement of said proximal bearing plates away from the distal bearing plate so as to increase their spacing from the distal bearing plate; and
    releasable locking devices each structured to selectively lock the distal bearing plate to a corresponding one of the first and second proximal bearing plates;
    wherein each releasable locking device has a first position that is engaged with both the distal bearing plate and the corresponding one of the first and second proximal bearing plates to maintain an initial distance therebetween;
    wherein each releasable locking device has a second position that is disengaged from one of the distal bearing plate and the corresponding one of the first and second proximal bearing plates to permit relative displacement of the corresponding one of the first and second proximal bearing plates away from the distal bearing plate to an increased distance therebetween; and
    wherein components of said ligament-tensioning device including the distal bearing plate, the first and second proximal bearing plates, and the displacer are dimensioned such that they can be accommodated between portions of the distal and proximal skeletal parts adjacent to the joint such that a joint capsule can be closed again while the components of the ligament-tensioning device are positioned in the joint capsule.

2. The device of claim 1, wherein the distal skeletal part is a tibia and the proximal skeletal part is a femur.

3. The device of claim 1, wherein the displacer comprises scissor-type guides that support the respective proximal bearing plates in a parallel position with respect to the distal bearing plate.

4. The device of claim 3, wherein the scissor-type guides are of torsionally stiff construction between the distal bearing plate and the respective proximal bearing plates to provide parallel guidance between the distal bearing plate and the proximal hearing plates that is precise in both the ventral-dorsal and the medial-lateral directions.

5. The device of claim 3, wherein said scissor-type guides comprise two scissor joints arranged close to opposite ends of said first and second proximal bearing plates.

6. The device of claim 5, wherein ends of the scissor joints are inserted in grooves in said distal and proximal bearing plates and one limb of each scissor joint or an end of one limb of each scissor joint is rotatably fixed within the distal and proximal bearing plates by bearing pins or slide pegs extending perpendicular to a run of said groove.

7. The device of claim 6, wherein on another end of the limb or at a free end of another limb there is provided a slide peg for guiding the respective limb or end in a groove in said distal or proximal bearing plate, which groove is formed to match the slide peg.

8. The device of claim 5, wherein said scissor joints are joined to one another at least by a connecting rod mounted at the end of a limb of each scissor joint.

9. The device of claim 1, wherein said first and second proximal bearing plates each comprise an upper and a lower part, the lower part comprising a mounting adapted to mount at least a portion of the displacer, the upper part being fixed releasably on the lower part to increase a thickness of the respective first and second proximal bearing plates.

10. The device of claim 1, further comprising a cylindrical recess or other second tool-engagement portion, provided on a side edge of the distal bearing plate or on side edges of the first and second proximal bearing plates for engagement of a positioning tool.

11. The device of claim 1, wherein the displacer comprises a drive element configured to drive the first and second proximal bearing plates away from the distal bearing plate; and
    wherein the drive element is configured such that it can be accommodated between the portions of the distal and proximal skeletal parts adjacent to the joint such that the joint capsule can be closed again while the ligament-tensioning device is positioned in the joint capsule.

12. The device of claim 11, wherein the drive element is entirely accommodated within a space between the distal bearing plate and the first and second proximal bearing plates.

13. The device of claim 12, wherein the drive element comprises a self-contained unit that does not require auxiliary energy to drive the first and second proximal bearing plates away from the distal bearing plate.

14. The device of claim 13, wherein the drive element comprises at least one spring element adapted to drive the first and second proximal bearing plates away from the distal bearing plate, the spring element configured to store a drive energy while in a starting state in which the first and second proximal bearing plates are spaced a minimum distance apart from the distal bearing plate, and to release the energy to increase the spacing when the device is actuated.

15. The device of claim 1, wherein the displacer comprises:
    a first spring element positioned between the distal bearing plate and the first proximal bearing plate and adapted to drive the first proximal bearing plate apart from the distal bearing plate and increase a spacing between the first proximal bearing plate and the distal bearing plate; and a second spring element positioned between the distal bearing plate and the second proximal bearing plate and adapted to drive the second proximal bearing plate apart from the distal bearing plate and increase a spacing between the second proximal bearing plate and the distal bearing plate independent of the spacing between the first proximal plate and the distal bearing plate.

16. The device of claim 15, wherein the first and second proximal bearing plates each overlap approximately one-half of the distal bearing plate.

17. The device of claim 15, wherein the releasable locking devices comprise:

a first releasable locking device engaged to the distal bearing plate and to the first proximal bearing plate for locking the first proximal bearing plate to the distal bearing plate at a first minimum spacing; and a second releasable locking device engaged to the distal bearing plate and to the second proximal bearing plate for locking the second proximal bearing plate to the distal bearing plate at a second minimum spacing.

18. The device of claim 15, wherein the displacer further comprises first and second scissor-type guides that support the first and second proximal bearing plates, respectively, in a parallel position with respect to the distal bearing plate.

19. The device of claim 1, wherein the displacer comprises an internal drive configured to force the first and second proximal bearing plates away from the distal bearing plate, and wherein the internal drive is entirely accommodated within a space between the distal bearing plate and the first and second proximal bearing plates.

20. the device of claim 1, wherein the releasable locking device comprises:

a first of the releasable locking devices structured to selectively and independently locking the distal bearing plate to the first proximal bearing plate; and a second of the releasable locking devices structured to selectively and independently lock the distal bearing plate to the second proximal bearing plate.

21. The device of claim 1, wherein each releasable locking device is pivotally mounted to one of the distal bearing plate and the corresponding one of the first and second proximal bearing plates and pivots between the first and second positions.

22. The device of claim 1, wherein each releasable locking device comprises a hook element.

23. A ligament-tensioning device for activation of a ligament and/or capsule system in the implantation of a joint implant, said device comprising:

a distal bearing plate adapted to bear against a distal skeletal part;

first and second proximal bearing plates, each of which at least partially overlaps said distal bearing plate when in a first in-use position, and adapted to bear against a proximal skeletal part;

a displacer for relative displacement of said proximal bearing plates away from the distal bearing plate so as to increase their spacing from the distal bearing plate; and releasable locking devices each structured to selectively lock the distal bearing plate to a corresponding one of the first and second proximal bearing plates;

wherein each releasable locking device has a first position that is engaged with both the distal bearing plate and the corresponding one of the first and second proximal bearing plates to maintain said minimum distance;

wherein each releasable locking device has a second position that is disengaged from one of the distal bearing plate and the corresponding one of the first and second proximal bearing plates to permit relative displacement of the corresponding one of the first and second proximal bearing plates away from the distal bearing plate to an increased distance therebetween;

wherein components of said ligament-tensioning device including the distal bearing plate, the first and second proximal bearing plates, and the displacer are dimensioned such that they can be accommodated between portions of the distal and proximal skeletal parts adjacent to the joint such that a joint capsule can be closed again while the components of the ligament-tensioning device are positioned in the joint capsule; and wherein said displacer comprises at least one spring element adapted to drive said proximal bearing plates, the spring element configured to store a drive energy while in a starting state in which said proximal bearing plates are spaced a minimum distance apart from said distal bearing plate, and to release said energy to increase the spacing when the device is actuated.

24. The device of claim 23, wherein said displacer has, assigned to each of said first and second bearing plates, a spring element for driving each of said proximal bearing plates.

25. The device of claim 23, wherein the at least one spring element is lockable.

26. The device of claim 23, wherein the at least one spring element comprises a compression spring element arranged in a region of overlap between said proximal and distal bearing plates.

27. The device of claim 26, wherein said at least one spring element comprises a spring selected from the group consisting of a steel helical spring and a titanium helical spring which has a form selected from the group consisting of a conical form and a double-cone form.

28. The device of claim 27, wherein said spring comprises a pitch indirectly proportional to a local winding diameter.

29. The device of claim 23, wherein said spring element comprises a flexural spring element.

30. The device of claim 29, wherein said spring element comprises a metal spring selected from the group consisting of a spiral spring and a leaf spring.

31. The device of claim 23, wherein the at least one spring element is matched in spring constant to a predetermined tensioning force.

32. The device of claim 23, wherein the at least one spring element provides a tensioning force that is substantially constant over its travel.

33. The device of claim 23, wherein the first and second proximal bearing plates each overlap approximately one-half of the distal bearing plate.

34. The device of claim 23, wherein the at least one spring element comprises:

a first spring element positioned between the distal bearing plate and the first proximal bearing plate and adapted to drive the first proximal bearing plate apart from the distal bearing plate and increase a spacing between the first proximal bearing plate and the distal bearing plate; and a second spring element positioned between the distal bearing plate and the second proximal bearing plate and adapted to drive the second proximal bearing plate apart from the distal bearing plate and increase a spacing between the second proximal bearing plate and the distal bearing plate independent of the spacing between the first proximal plate and the distal bearing plate.

35. The device of claim 34, wherein the first and second proximal bearing plates each overlap approximately one-half of the distal bearing plate.

36. The device of claim 34, wherein the releasable locking devices comprise:
a first releasable locking device engaged to the distal bearing plate and to the first proximal bearing plate for locking the first proximal bearing plate to the distal bearing plate at a first minimum spacing; and
a second releasable locking device engaged to the distal bearing plate and to the second proximal bearing plate for locking the second proximal bearing plate to the distal bearing plate at a second minimum spacing.

37. The device of claim 34, wherein the displacer further comprises first and second scissor-type guides that support the first and second proximal bearing plates, respectively, in a parallel position with respect to the distal bearing plate.

38. The device of claim 23, wherein each releasable locking device is pivotally mounted to one of the distal bearing plate and the corresponding one of the first and second proximal bearing plates and pivots between the first and second positions.

39. A ligament-tensioning device for activation of a ligament and/or capsule system in the implantation of a joint implant, said device comprising:
a distal bearing plate adapted to bear against a distal skeletal part;
first and second proximal bearing plates, each of which at least partially overlaps said distal bearing plate when in a first in-use position, and adapted to bear against a proximal skeletal part; and
a displacer for relative displacement of said proximal bearing plates away from the distal bearing plate so as to increase their spacing from the distal bearing plate;
wherein components of said ligament-tensioning device including the distal bearing plate, the first and second proximal bearing plates, and the displacer are dimensioned such that they can be accommodated between portions of the distal and proximal skeletal parts adjacent to the joint such that a joint capsule can he closed again while the components of the ligament-tensioning device are positioned in the joint capsule;
wherein the distal bearing plate or the first and second proximal bearing plates comprise releasable locking devices for independent locking of said first and second proximal bearing plates to said distal bearing plate at a minimum spacing and with respect thereto;
wherein the releasable locking devices each have a first position that is engaged with both the distal bearing plate and a corresponding one of the first and second proximal bearing plates to maintain the minimum spacing;
wherein the releasable locking devices each have a second position that is disengaged from one of the distal bearing plate and the corresponding one of the first and second proximal bearing plates to permit relative displacement of the corresponding one of the first and second proximal bearing plates away from the distal bearing plate to an increased spacing; and
wherein the releasable locking devices are each pivotally mounted to one of the distal bearing plate and the corresponding one of the first and second proximal bearing plates and pivot between the first and second positions.

40. The device of claim 39, wherein the releasable locking devices comprise:
a first releasable locking device engaged to the distal bearing plate and to the first proximal bearing plate for locking the first proximal bearing plate to the distal bearing plate at a first minimum spacing; and
a second releasable locking device engaged to the distal bearing plate and to the second proximal bearing plate for locking the second proximal bearing plate to the distal bearing plate at a second minimum spacing.

41. The device of claim 40, wherein the displacer comprises:
a first spring element positioned between the distal bearing plate and the first proximal bearing plate and adapted to drive the first proximal bearing plate apart from the distal bearing plate; and
a second spring element positioned between the distal bearing plate and the second proximal bearing plate and adapted to drive the second proximal bearing plate apart from the distal bearing plate.

42. The device of claim 39, wherein the displacer comprises an internal drive configured to force the first and second proximal bearing plates away from the distal bearing plate, and wherein the internal drive is entirely accommodated within a space between the distal bearing plate and the first and second proximal bearing plates.

43. A ligament-tensioning device for activation of a ligament and/or capsule system in the implantation of a joint implant, said device comprising:
a distal bearing plate adapted to bear against a distal skeletal part;
first and second proximal bearing plates, each of which at least partially overlaps said distal bearing plate when in a first in-use position, and adapted to bear against a proximal skeletal part; and
a displacer for relative displacement of said proximal bearing plates away from the distal bearing plate so as to increase their spacing from the distal bearing plate;
wherein components of said ligament-tensioning device including the distal bearing plate, the first and second proximal bearing plates, and the displacer are dimensioned such that they can be accommodated between portions of the distal and proximal skeletal parts adjacent to the joint such that a joint capsule can be closed again while the components of the ligament-tensioning device are positioned in the joint capsule;
wherein the distal bearing plate or the first and second proximal bearing plates comprise releasable locking devices for independent locking of said first and second proximal bearing plates to said distal bearing plate at a minimum spacing and with respect thereto; and
wherein each of said releasable locking devices has a hook pivotally mounted on one of the distal and first and second proximal bearing plates and engaging in an opposing one of the distal and first and second proximal bearing plates, on which hook there is provided a first tool-engagement portion for actuation.

44. The device of claim 43, wherein the first tool-engagement portion is formed for engagement of a hex key.

45. The device of claim 43, wherein in the material of said first and second proximal bearing plates, in spatial association with the hook articulated on said distal bearing plate, there is formed an engagement portion for the hook.

46. The device of claim 43, wherein a first bearing peg of a scissor joint of the first or second proximal bearing plate projects beyond an outer edge thereof and is so arranged relative to the hook pivotally mounted on said distal bearing plate that it forms a counter-bearing of the locking device.

47. The device of claim 46, wherein a second bearing peg of a scissor joint of said first or second proximal bearing plates projects beyond the outer edge thereof and is so arranged relative to the hook pivotally mounted on said distal bearing plate that it forms a hinge pin thereof.

48. A ligament-tensioning device for activation of a ligament and/or capsule system in the implantation of a joint implant, said device comprising:
- a distal bearing plate adapted to bear against a distal skeletal part;
- first and second proximal bearing plates, each of which at least partially overlaps said distal bearing plate when in a first in-use position, and adapted to bear against a proximal skeletal part; and
- a displacer for relative displacement of said proximal bearing plates away from the distal bearing plate so as to increase their spacing from the distal bearing plate;
- wherein components of said ligament-tensioning device including the distal bearing plate, the first and second proximal bearing plates, and the displacer are dimensioned such that they can be accommodated between portions of the distal and proximal skeletal parts adjacent to the joint such that a joint capsule can be closed again while the components of the ligament-tensioning device are positioned in the joint capsule;
- wherein the distal bearing plate or the first and second proximal bearing plates comprise releasable locking devices for independent locking of said first and second proximal bearing plates to said distal bearing plate at a minimum spacing and with respect thereto; and
- wherein the releasable locking devices each comprise a hook element pivotally mounted on one of the distal and proximal bearing plates and releasably engaging an opposing one of the distal and proximal bearing plates.

* * * * *